United States Patent
Paul et al.

(10) Patent No.: US 6,795,190 B1
(45) Date of Patent: Sep. 21, 2004

(54) ABSORPTION SPECTROSCOPY INSTRUMENT WITH OFF-AXIS LIGHT INSERTION INTO CAVITY

(75) Inventors: Joshua B Paul, Brookline, MA (US); James J Scherer, San Mateo, CA (US); Anthony O'Keefe, Cupertino, CA (US)

(73) Assignee: Los Gatos Research, Inc., Mountain View, CA (US)

( * ) Notice: Subject to any disclaimer, the term of this patent is extended or adjusted under 35 U.S.C. 154(b) by 445 days.

(21) Appl. No.: 09/976,549

(22) Filed: Oct. 12, 2001

(51) Int. Cl.⁷ .............................................. G01N 21/00
(52) U.S. Cl. ..................................... 356/437; 356/440
(58) Field of Search ............................... 356/432–440, 356/454

(56) References Cited

U.S. PATENT DOCUMENTS

| | | | |
|---|---|---|---|
| 4,793,709 A | 12/1988 | Jabr et al. | 356/445 |
| 5,291,265 A * | 3/1994 | Kebabian | 356/246 |
| 5,528,040 A | 6/1996 | Lehmann | 250/343 |
| 5,912,740 A | 6/1999 | Zare et al. | 356/437 |

OTHER PUBLICATIONS

J.B. Paul et al., "Ultrasensitive Absorption Spectroscopy with a High–Finesse Optical Cavity and Off–Axis Alignment", *Applied Optics*, vol. 40, No. 27, Sep. 20, 2001, pp. 4904–4910.

D. R. Herriott et al., "Folded Optical Delay Lines", *Applied Optics*, 1965, vol. 4, No. 8, pp. 883–889.

K. K. Lehmann et al., "The Superposition Principle and Cavity Ring–Down Spectroscopy", *J. Chem. Phys.* 1996, vol. 105, No. 23, pp. 10263–10277.

G. Meijer et al., "Coherent Cavity Ring Down Spectroscopy", *Chemical Physics Letters*, 1994, vol. 217, No. 1,2, pp. 112–116.

D.Z. Anderson et al., "Mirror Reflectometer Based on Optical Cavity Decay Time", *Applied Optics*, 1984, vol. 23, No. 8, pp. 1238–1245.

A. O'Keefe et al., "CW Integrated Cavity Output Spectroscopy", *Chemical Physics Letters*, 1999, vol. 307 (5–6), pp. 343–349.

D. Herriott et al., "Off–Axis Paths in Spherical Mirror Interferometers", *Applied Optics*, 1964, vol. 3, No. 4, pp. 523–526.

J. Ye et al., "Ultrasensitive Detections in Atomic and Molecular Physics: Demonstration in Molecular Overtone Spectrocopy", *J. Opt. Soc. Am. B.*, vol. 15, No. 1, 1998, pp. 6–15.

B.A. Paldus et al., "Cavity–Locked Ring–Down Spectroscopy", *Journal of Applied Physics*, 1998, vol. 83, No. 8, pp. 3991–3997.

(List continued on next page.)

*Primary Examiner*—Frank G. Font
*Assistant Examiner*—Amanda Merlino
(74) *Attorney, Agent, or Firm*—Thomas Schneck; Mark Protsik

(57) ABSTRACT

This patent describes a new method and apparatus which allows optical cavities to be used simply and effectively as absorption cells for the purpose of performing sensitive absorption spectroscopy. This method introduces a continuous-wave light beam into the cavity using an off-axis cavity alignment geometry to systematically eliminate the resonances commonly associated with optical cavities, while preserving the absorption signal amplifying properties of such cavities. This reduces the complexity of the apparatus considerably compared with other optical cavity-based absorption methods when applied in conjunction with either cavity ringdown spectroscopy or integrated cavity output spectroscopy. This method can also be used to characterize other optical loss processes occurring within the cavity such as scattering or total extinction coefficients, and to determine the losses due to the cavity mirrors themselves (reflectometry).

40 Claims, 4 Drawing Sheets

OTHER PUBLICATIONS

A. O'Keefe et al., "Cavity Ring–Down Optical Spectrometer for Absorption Measurements Using Pulsed Laser Sources", *Review of Scientific Instruments,* 1988, vol. 59, No. 12, pp. 2544–2551.

D.A. Jackson, "The Spherical Fabry–Perot Interferometer as an Instrument of High Resolving Power for use with External or with Internal Atomic Beams", *Proc. of Royal Soc.,* London, Ser. A., 1961, vol. 263, pp. 289–308.

J.J. Scherer et al., "Cavity Ringdown Laser Absorption Spectroscopy: History, Development, and Application to Pulsed Molecular Beams", *Chemical Reviews,* 1997, vol. 97, No. 1, pp. 25–51.

D. Ramanini et al., "Diode Laser Cavity Ring Down Spectroscopy", *Chemical Physics Letters,* 1997, vol. 270, No. 5–6, pp. 538–545.

* cited by examiner

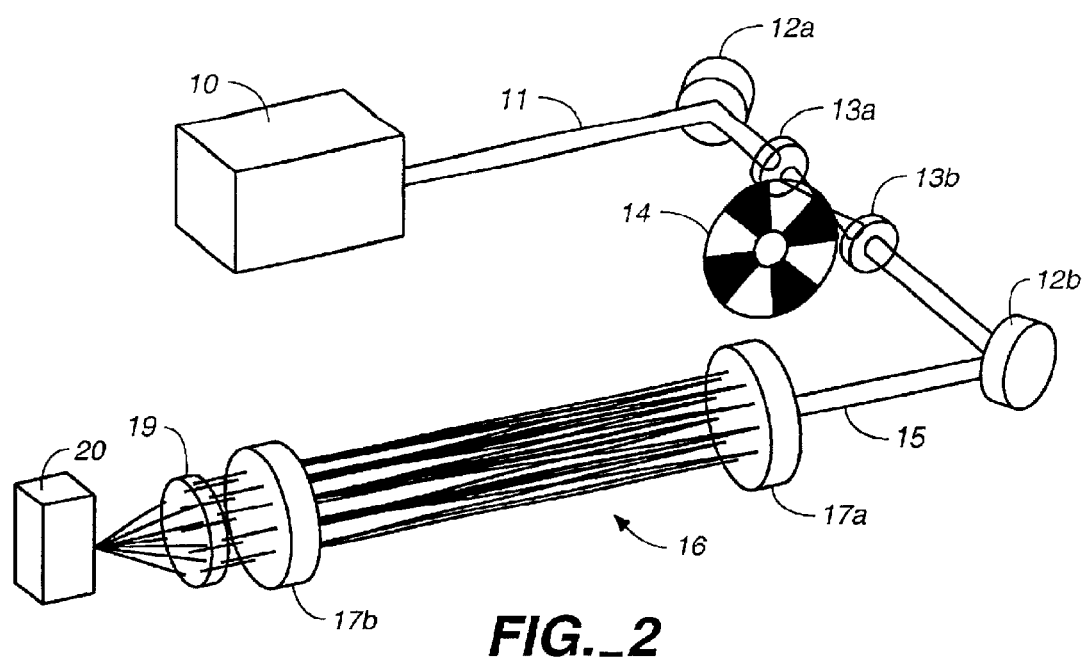
FIG._2
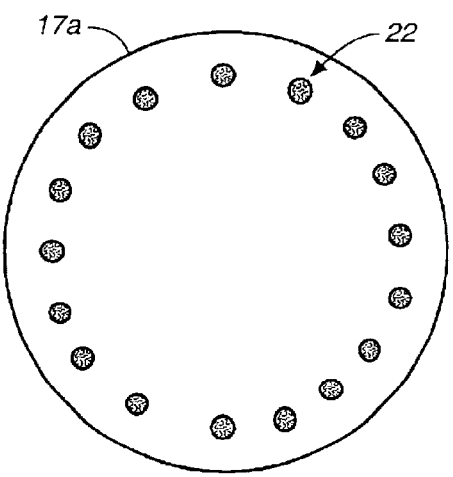
FIG._3A
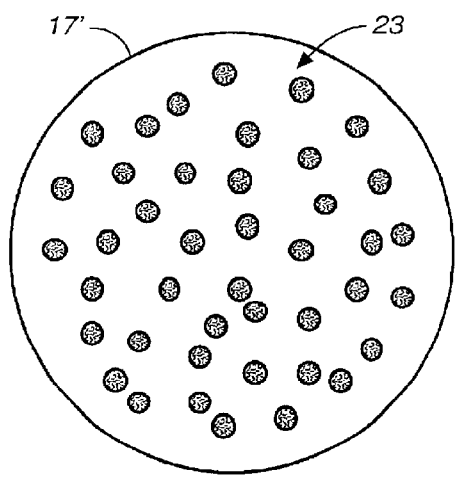
FIG._3B

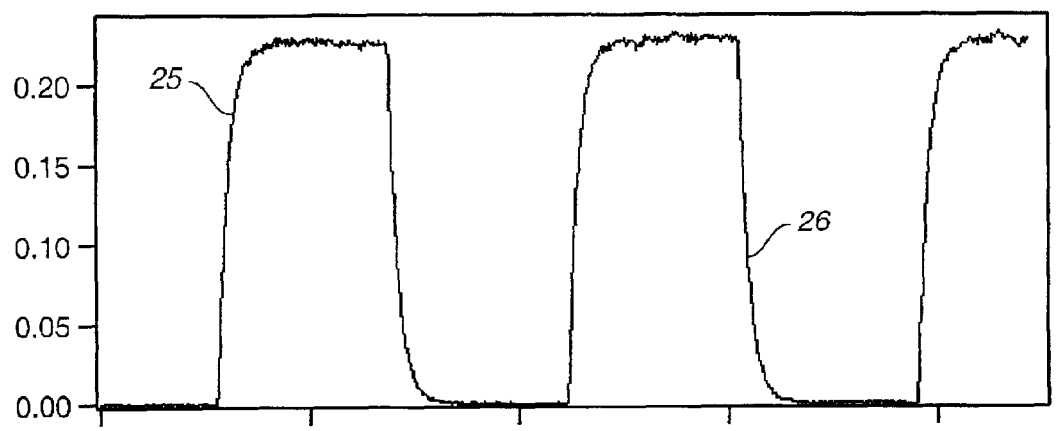
FIG._4
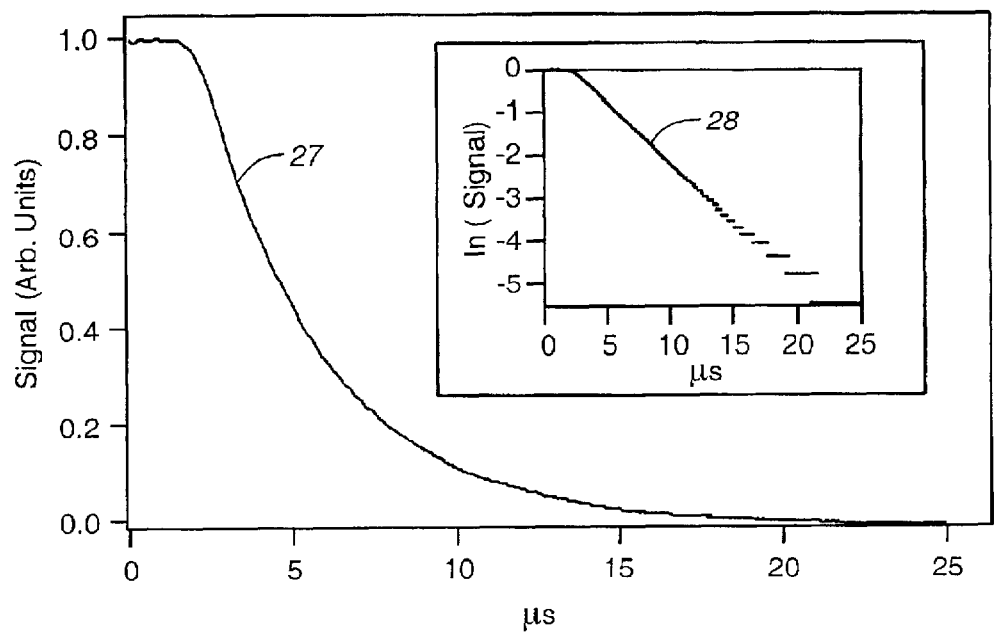
FIG._5

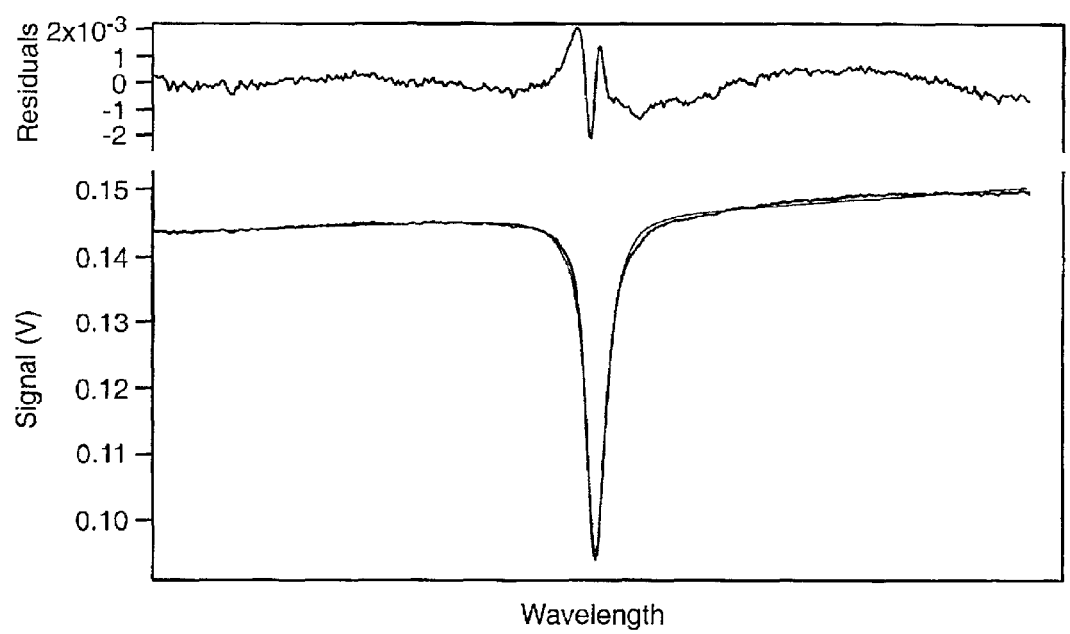
FIG._6

ABSORPTION SPECTROSCOPY INSTRUMENT WITH OFF-AXIS LIGHT INSERTION INTO CAVITY

STATEMENT REGARDING FEDERALLY SPONSORED RESEARCH AND DEVELOPMENT

This invention was made with Government support under contract number NAS2-01035, NAS2-01044, and NAS5-01056 awarded by National Aeronautics and Space Administration. The Government has certain rights in the invention.

TECHNICAL FIELD

The present invention relates to absorption spectroscopy methods and apparatus, and in particular to those methods and apparatus which employ an optical cavity for increasing detection sensitivity, especially ones adapted for cavity ring-down spectroscopy (CRDS) and integrated cavity output spectroscopy (ICOS). Arrangements, active or passive, for reducing sensitivity of the instrument to alignment or vibrations, including those that manipulate or control optical resonances of the instrument's cavity are particularly relevant.

BACKGROUND ART

Cavity ringdown spectroscopy (CRDS) and integrated cavity output spectroscopy (ICOS) methods and associated instruments employ optical cavities (also known as "etalons") as absorption cells for spectroscopic purposes. These spectroscopy methods and instruments have a broad range of other applications, such as characterizing mirror reflectivities, determining optical cavity losses (including scattering, absorption, etc.) and measuring thin film absorption. Other potential uses include using the invention for quantitative chemical analysis systems for applications such as offgas monitoring, medical diagnostics (such as breath analysis), trace gas analysis, thin film analysis, pollution monitoring, process control monitoring, purity analysis, and toxic chemicals detection. Although the background discussion will focus on the specific development of absorption techniques for gas phase chemical detection and characterizing optical components such as high reflectivity, low loss mirrors, it is by no means limited to this application.

The state of the art in spectrophotometer technology and spectroscopic techniques used for the purpose of spectrally characterizing solids, liquids, and gases includes absorption, emission, and ionization-based techniques. Recent developments in optical components and spectrally bright light sources have led to a variety of spectroscopic-based techniques and instruments that provide chemical analysis data of gaseous samples. Conventional Absorption (CA) or Emission (EM) spectroscopies are currently implemented for the quantitative analysis of chemical species in gases as a means of providing concentration information, but these methods frequently require tedious calibration procedures (EM) or suffer from low sensitivity. In the case of emission spectroscopy, inter and intramolecular dynamics, such as internal conversion or predissociation, can significantly degrade the ability to both detect and quantify species concentrations. Although much less effected by these dynamical processes, CA historically suffers from lower sensitivity (compared to that of EM, for example), and hence cannot typically achieve similar detection sensitivities. Another technology currently in use for chemical monitoring is Laser Spark Spectroscopy (LS), which involves measuring emission spectra of species that are vaporized with an intense laser pulse. Although highly sensitive, LS is only capable of identifying the presence of metals, and is not generally capable of providing absolute concentrations for those species without elaborate calibration procedures. A primary reason for employing CA is the relative ease with which absolute species concentration can be determined from the associated absorption spectra. To circumvent the historically lower sensitivity of absorption spectroscopy, several methods have been developed. Absorption-based optical detection methods which enable chemical concentrations to be determined include frequency (or amplitude) modulated laser absorption spectroscopy (FM-LAS) and Fourier transform spectroscopy (FTS). Although these methods have been used with some success, they can suffer from low sensitivity (FTS), or can be difficult or impossible to implement in spectrally congested areas and have limited spectral coverage (FM-LAS).

An alternative to these methods involves the use of high finesse optical cavities, which have long been known to amplify optical loss processes occurring between the cavity optics. (Jackson, D. A., *The Spherical Fabry-Perot Interferometer as an Instrument of High Resolving Power for use with External or with Internal Atomic Beams*. Proc. R. Soc. London Ser. A, 1961. 263: p. 289.) Ultimately, this allows highly sensitive measurements of such processes as molecular absorption to be achieved. Several methods have been described to use optical cavities for such purposes. (Scherer, J. J., et al., *Cavity ringdown laser absorption spectroscopy—history, development, and application to pulsed molecular beams*. Chemical Reviews, 1997 January–February. 97(1): p. 25–51. Romanini, D., A. A. Kachanov, and F. Stoeckel, *Diode laser cavity ring down spectroscopy*. Chemical Physics Letters, 30 May 1997. 270(5–6): p. 538–45. Ye, J., L.-S. Ma, and J. L. Hall, *Ultrasensitive detections in atomic and molecular physics: demonstration in molecular overtone spectroscopy*. J. Opt. Soc. Am. B, 1998. 15(1): p. 6. Paldus, B. A., et al., *Cavity-locked ring-down spectroscopy*. Journal of Applied Physics, 15 Apr. 1998. 83(8): p. 3991–7.) One of the most common, known as cavity ringdown spectroscopy (CRDS), measures the total optical cavity loss by monitoring the decay of the intracavity intensity following the injection of radiation into the cavity, either by a single laser pulse, (O'Keefe, A. and D. A. G. Deacon, *Cavity ring-down optical spectrometer for absorption measurements using pulsed laser sources*. Review of Scientific Instruments, December 1988. 59(12): p. 2544–51.) or by an abruptly interrupted continuous-wave (CW) laser. (Anderson, D. Z., J. C. Frisch, and C. S. Masser, *Optical reflectometer based on optical decay time*. Appl. Opt., 1984. 23: p. 1238.) The ringdown process itself was patented by Litton Corporation (U.S. Pat. No. 4,793,709, Method and apparatus for measuring losses of an optical cavity, issued Dec. 27, 1988, now expired.) for the specific purpose of determining mirror reflectivities. Since this patent, CRDS has been developed (and extensively published in the open literature) for the specific purpose of determining atomic and molecular absorption for species located within the optical cavity (between the mirrors). The currently well established and practiced pulsed CRDS method was first developed by O'Keefe and Deacon in 1988, who demonstrated its high sensitivity and spectroscopic capabilities by measuring weak visible absorption by molecular oxygen. (O'Keefe, A. and D. A. G. Deacon, *Cavity ring-down optical spectrometer for absorption measurements using pulsed laser sources*. Review of Scientific Instruments, December 1988. 59(12): p. 2544–51.) Additionally, continuous-wave versions of CRDS that are based on the original, early versions of the technology have been developed for the specific task of obtaining absorption spectra of chemical species placed in the cavity. (U.S. Pat. No. 5,528,040, *Ring-down cavity spectroscopy cell using continuous wave excitation for trace species detection*, Jun. 18, 1996.) Other cavity-based methods, such as integrated cavity output spectroscopy (ICOS) (O'Keefe, A., J. J. Scherer, and J. B. Paul, *CW integrated cavity output spectroscopy*. Chemical Physics Letters, 9 Jul. 1999. 307(5–6): p. 343–9.) and noise-immune cavity-enhanced optical heterodyne molecular spectroscopy (NICE-OHMS) (Ye, J., L.-S. Ma, and J. L. Hall, *Ultrasensitive detections in atomic and molecular physics: demonstration in molecular overtone spectroscopy*. J. Opt. Soc. Am. B, 1998. 15(1): p. 6.) use the cavity transmission properties to gauge the intracavity loss, but in these cases the intrinsic cavity loss must be determined separately, by using CRDS for example, to obtain quantitative absorption intensity data.

Many of the above methods, in particular those employing narrowband CW laser sources, are designed to manipulate or control the optical resonances that arise within cavity due to the periodic boundary conditions imposed on the intracavity electric field by the mirror surfaces. These resonances, which are interferometric in nature, comprise the general subject of Fabry-Perot theory. To control them precisely requires complex and expensive instrumentation and hardware, and places extreme constraints on the overall stability of the apparatus.

One solution to the problem of mode-buildup within the cavity involved intentionally creating a dense transverse cavity mode spectrum by employing particular cavity lengths that ensured a frequency spread among the various transverse modes, thereby filling in the region of the spectrum falling between the longitudinal cavity modes. (Meijer, G., et al., *Coherent cavity ring down spectrometry*. Chemical Physics Letters, 7 Jan. 1994. 217(1,2): p.112–6.) While the laser was aligned on-axis with the cavity, it was also slightly divergent upon entering the cavity to ensure transverse mode overlap. While similar, we believe this approach to be inferior to that presented below primarily for two reasons. Firstly, with their approach, light at different frequencies takes different paths through the cavity, while with the approach described below all of the light takes substantially the same path. Different light paths are subject to different levels of optical intensity loss due to such factors as variations in the mirror surface and diffraction at the edges of the mirrors. Therefore, our approach should provide an inherently smoother frequency response from the cavity. Secondly, we believe our off-axis approach is more capable of creating the densest possible cavity mode spectrum. This aspect is critical to the success of the method, as the goal is to create a virtual continuum of modes in order to completely flatten the optical frequency response of the cavity.

DISCLOSURE OF THE INVENTION

The solution represented by the present invention utilizes off-axis paths through spherical or astigmatic mirror interferometers to systematically disrupt these resonances, rather than attempting to manipulate them in other ways. The goal is to remove the frequency selectivity of the cavity, or to effectively decrease the cavity Longitudinal mode spacing such that a nearly continuous cavity transmission spectrum results, rendering it effectively a broadband device. This approach offers the following advantages over previous methods. Most importantly, narrowband lasers ($\Delta\nu<100$ MHz) can be used without actively controlling the cavity length. This eliminates the need for expensive components such as piezo-electric transducers, lock-in amplifiers, acousto-optic modulators, etc. Additionally, this design reduces the optical feedback from cavity to the source laser, which is particularly important for the case of a distributed-feedback diode laser sources. Previously, either Faraday isolators, which are expensive and not available over much of the infrared spectrum, or three-mirror ring-cavities (U.S. Pat. No. 5,912,740, Ring-resonant cavities for spectroscopy, Jun. 15, 1999.) have been used for this purpose. Finally, the constraints on the overall system alignment are vastly reduced. Rather than only a single possible alignment geometry (i.e. the laser on-axis with the cavity), any stable path (see below) through the cavity can be used. This allows simpler alignment routines, and lowers the sensitivity of the instrument to vibration. Off-axis cavity ringdown spectroscopy (OA-CR) and off-axis integrated cavity output spectroscopy (OA-I) methods and associated instruments allow high finesse optical cavities (also known as "etalons") to be used as absorption cells for spectroscopic purposes with significantly reduced complexity compared with previous approaches.

BRIEF DESCRIPTION OF THE DRAWINGS

FIG. 2 is a schematic perspective view of an absorption spectrometer apparatus with off-axis light injection into the optical cavity according to the present invention. The apparatus can operate in both a cavity ringdown mode (OA-CR) and an integrated cavity output mode (OA-I) depending on whether the beam chopping element of the apparatus is active.

FIGS. 3a and 3b represent examples of possible multipass patterns that can be seen on the rear cavity mirror (17b). This illustrates the effect of the multipass cavity alignment of the present invention, for the case of spherical cavity mirrors (FIG. 3a) and astigmatic cavity mirrors (FIG. 3b), respectively.

FIG. 4 is a graph of measured cavity output versus time, with the chopper in the FIG. 2 apparatus activated, showing resulting cavity buildup and ringdown cycles with a light absorbing sample present in the cavity.

FIG. 5 is a graph of normalized ringdown decay signal, and an inset graph of the corresponding natural logarithm of the signal, both with respect to time, for the cavity cycles of FIG. 4 (the FIG. 5 decay signal is an average over 20 decay events from the FIG. 4 data).

FIG. 6 is a graph of measured cavity output versus laser wavelength using the apparatus of FIG. 2 with a light absorbing sample present in the cavity (a rotationally resolved line of the molecular Carbon Dioxide combination band near 1.6 microns wavelength is shown), as measured in OA-I (chopper inactive). The measurements correspond to the HITRAN prediction based on an 0.1 Bar sample of pure $CO_2$ and a pathlength of 10000 meters. The difference between the measured spectra and the fit is shown above.

BEST MODE OF CARRYING OUT THE INVENTION

Figure 1:
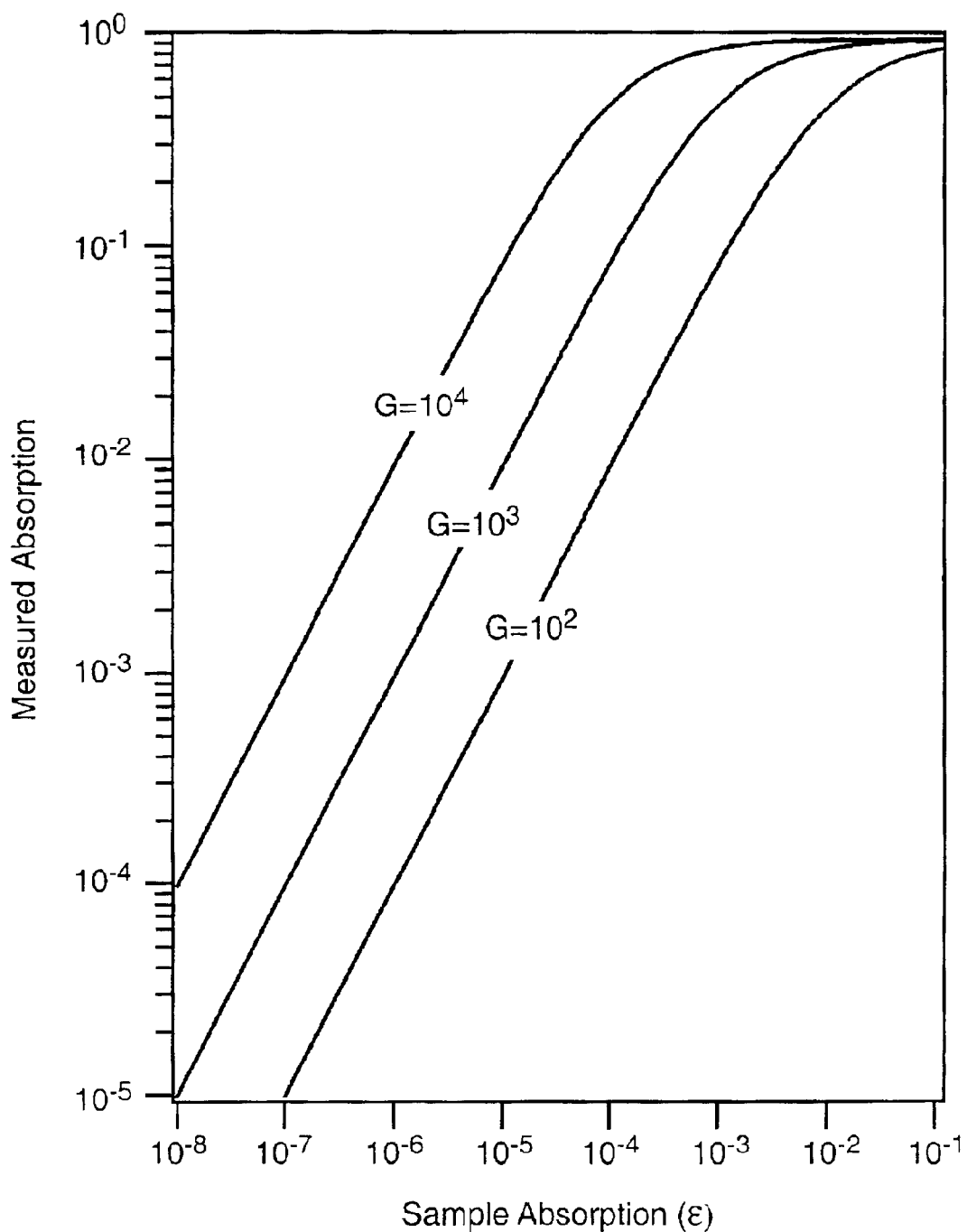
FIG. 1 is a graph of the effective cavity gain (measured absorption) as a function of the cavity's gain parameter G and the intracavity absorption (single pass sample absorption) for an absorption spectrometer in accord with the present invention.

Off-axis paths through optical cavities are well understood, (Herriott, D., H. Kogelnik, and R. Kompfner,

*Off-Axis Paths in Spherical Mirror Interferometers.* Applied Optics, April 1964. 3(4): p. 523–26. Herriot, D. R. and H. J. Schulte, *Folded Optical Delay Lines.* Applied Optics, 1965. 4(8): p. 883–89.) and in effect spatially separate the multiple reflections within the cavity until such time that the "reentrant condition" is fulfilled, referring to the time during which the ray begins to retrace its original path through the cavity. The occurrence of this condition is dictated by the specific mirror curvature and spacing of the mirrors forming the cavity. Any stable cavity geometry can produce stable off-axis paths through the cavity, where the stability condition (for a spherical 2-mirror cavity) is defined by the inequality $$0<(1-d/R_1)(1-d/R_2)<1, \qquad (1)$$

where d is the mirror spacing and $R_1$ and $R_2$ are the mirror radii of curvature. The multiple reflections appear on the mirrors as a series of spots in an elliptical pattern. The per-pass rotation ($\theta$) around the ellipse is again determined purely by the geometry of the cavity, and is given by $$\cos \theta = 1 - d/R, \qquad (2)$$

assuming $R=R_1=R_2$. When $2m\theta = 2\pi n$, where m equals the number of optical round-trip passes and n is an arbitrary integer, the pattern becomes re-entrant. For certain cases, this occurs after only a few passes, however, for others the number of passes can be unbounded. In many respects, the properties of the cavity, including the free spectral range (FSR), become similar to one that is m times longer. For example, a 0.5 m cavity normally has a FSR of 300 MHz, however, when the cavity is aligned in a 100 pass configuration (50 round-trips) it has a FSR of only 6 MHz. The reentrant condition can easily be lengthened to over 1000 passes by using astigmatic mirrors, which results in a Lissajous spot pattern. (Herriot, D. R. and H. J. Schulte, *Folded Optical Delay Lines.* Applied Optics, 1965. 4(8): p. 883–89.) For the cases of OA-CR and OA-I, since the light is not extracted from the cavity by means of a hole in the mirror, a specific pattern (or even a known pattern) is not required. This fact removes much of the complications associated with astigmatic mirror cavities.

Once a condition is achieved where the effective cavity FSR is significantly narrower than the laser bandwidth, the "fringe contrast" ratio approaches unity, implying that the energy coupled into the cavity ceases to be a function of the laser wavelength. (Lehmann, K. K. and D. Romanini, *The superposition principle and cavity ring-down spectroscopy.* J. Chem. Phys., 1996. 105(23): p. 10263.) In practice, the more important ratio is between the cavity FSR and the bandwidth of absorption feature of interest, as even if the above condition is not met, as long as the effective FSR is narrower than the absorption feature, the laser frequency can be either dithered or simply rapidly scanned through the cavity modes to reduce the fringe contrast while retaining a sufficient number of data points to define the absorption feature.

With these conditions met, all wavelength and electric-field phase information can be neglected, leading to a simplified description of the intracavity optical intensity. Here, a source term is added to the standard differential equation used to describe the ringdown event, (Scherer, J. J., et al., *Cavity ringdown laser absorption spectroscopy— history, development, and application to pulsed molecular beams.* Chemical Reviews, 1997 January–February. 97(1): p. 25–51.) resulting in the following rate equation describing the change in the intracavity power (traveling in each direction):

$$\frac{dI}{dt} = \frac{c}{2L}[I_L C_p T - 2I(1-R)], \qquad (3)$$

where $I_L$ is the incident laser power, $C_p$ is a cavity coupling parameter, R and T are the mirror intensity reflection and transmission coefficients, L is the cavity length, and c is the speed of light. The factor of 2 in the loss term accounts for the fact that the light leaves through both mirrors, while only enters through one. $C_p$ has a value between 0 and 1, and generally depends on the mode quality of the light source and the degree of mode matching between the cavity and the laser. For pulsed lasers, this value is often fairly low (~0.1), but it can approach unity for a well matched $TEM_{00}$ CW laser. Assuming a stable (i.e. time invariant) light source, the solution to Eq. 3 for an initially empty cavity is $$I = \frac{I_L C_p T}{2(1-R)}\left(1 - e^{\frac{-1}{\tau}}\right). \qquad (4)$$

When the laser is switched on, a "ring-up" occurs with the same time-constant as the ring-down, given by $\tau = L/(c(1-R))$. Steady-state is reached when $I = I_L C_p T/(2(1-R))$ in each direction, i.e. the amount transmitting through the rear mirror is $\approx I_L C_p T/2$ (assuming $R+T \approx 1$). In other words, at steady-state half of the laser power coupling into the cavity leaves through each mirror, as required by energy conservation. In general, this result represents the broadband steady-state transmission of any high finesse etalon, as it also corresponds to the integral of the Airy function over one FSR. Once sufficient laser power is leaving the cavity, the laser can be quickly interrupted to observe the ringdown decay. As the intensity buildup occurs predictably and on a well-defined timescale, this can be done with an passive device such as a mechanical chopper. Alternative chopping schemes may employ active devices such as acousto-optic modulators, or Pockels cells, tuning forks, or simply current or power modulation of the laser source.

With an absorbing medium between the mirrors, R is replaced by R', given by $$R' = R \cdot e^{-\alpha(\omega)}, \qquad (5)$$

where $\alpha(\omega)$ represents the absorbance of the medium over the length of the cavity. Thus, the intracavity absorption can be determined by comparing the cavity decay times with and without the absorber present, as comparing Eq. (5) with the Beer-Lambert absorption formula ($I/I_o = e^{-\alpha(\omega)}$) reveals that $I/I_o = R'/R$ on a per-pass basis. Eqs. (4) and (5) also show that absorption information is contained in the steady-state cavity output intensity, which is the basis for ICOS. From these equations, it is easy to show that the change in steady-state output due to the presence of an absorbing species is given by $$\frac{\Delta I}{I} = \frac{GA}{1+GA}, \qquad (6)$$

where $A = 1 - e^{\alpha(\omega)}$ and $G = R/(1-R)$. For weak absorption (GA<<1), the cavity provides a linear absorption signal gain (FIG. 1). Therefore, G will be referred to as the gain of the cavity. Physically, G equals the number of optical passes occurring within cavity decay time ($G \approx \tau c/L$), and is also simply related to the cavity finesse (G≈F/π). For example, a gain of $10^4$ (1−R=100 ppm) would result in a 1% change in cavity output power for an absorption (A) of 1 ppm. It is also clear from FIG. 1 that as the absorption becomes comparable to the intrinsic cavity loss, the gain rolls-off due to a saturation effect.

The above analysis shows that the cavity provides tremendous signal gains even if the resonances are completely suppressed. The transmitted power level, on the other hand, is reduced by a factor of ~T/2, or $2·10^4$ for of the case of T=100 ppm mirrors. Due to this, powerful lasers and sensitive detectors are certainly desirable to achieve high sensitivity with this method. In terms of the ultimately achievable shot-noise limit, however, the difference between the two methods is only $\sqrt{T}/2$ for a given laser power level, or a factor of 140 in this case.

DETAILED DESCRIPTION OF THE PREFERRED EMBODIMENT AND MODES OF OPERATION

A schematic diagram of the presently preferred embodiment of the apparatus of the present invention is shown in FIG. 2. An external cavity diode laser 10 emits a laser beam 11 that is directed by folding mirrors 12a and 12b to an optical cavity 16. The optical cavity 16 consisted of two identical 6 m. radius of curvature, 1 in. (25 mm) diameter mirrors 17a and 17b, spaced 67 cm. Apart. Preferably, the mirror reflectivities are higher than 0.99. However, reflectivities as low as 0.5 could be used. These parameters may be varied significantly without materially affecting the method. The use of long focal length optics compared with the cavity length was chosen following numerical simulations of a variety of cavity designs, including near confocal, and the commonly used spacing near the limit of stability of slightly less than 4f, where f equals the mirror focal length. While each of these possibilities could be used to create a dense cavity mode spectrum, the long focal length condition was found to be the least sensitive to changes in both alignment and mirror spacing. Additionally, the pattern of light emerging from such a cavity could be most easily focused to a small area. While this is not a big concern when large area photomultiplier tubes are available, it becomes important for infrared applications where small detector element sizes are preferred to reduce noise.

The mirrors 17a and 17b provided a per mirror intensity loss R (G≈1/(1−R)) at a wavelength λ. The ringdown cavity 16 and a light source such as an external cavity diode laser (ECDL) 10 can be mode matched using a two lens telescope (lenses 13a and 13b). A means of interrupting the beam of light, such as a standard mechanical chopper 14 placed at the focal point between the telescope lenses 13a and 13b, interrupts the beam 11 at some repetition rate. This arrangement provides a shut-off time of the chopped laser beam 15 into the cavity 16 that is significantly less than the optical lifetime of the cavity as determined by the mirror losses and the effects of absorption and scatter in the medium between the mirrors. The embodiment can carry out a cavity ringdown method when the apparatus' mechanical chopper 14 is rotated, or equivalently when some other method of interrupting the light beam is employed. The embodiment alternatively can carry out an ICOS method when the beam is not interrupted. Light exiting the cavity 16 is focused by a lens 19, filtered by a narrow band-pass interference filter and detected by a photomultiplier tube (PMT) 20. Any fast light detector, such as a photodiode detector, can be used in replacement of the photomultiplier tube, 20, to perform time domain cavity ringdown. In the ICOS embodiment, the detector does not require fast time response.

A. Off-Axis Injection

FIG. 3a shows a typical pattern of light spots that would be observed by a video camera through the rear cavity mirror 17b when a visible laser is used to inject light into the cavity. The pattern 22 in FIG. 3a closely matches that expected from theoretical models, although in practice individual spots are not observed because the resulting image is actually the sum of thousands of slightly displaced spots, only a few of which are shown. With slightly astigmatic mirrors 17', a Lissajous pattern 23 (FIG. 3b) is observed. Here, the effective reentrant condition is lengthened compared with the spherical case, resulting in an even closer cavity mode spacing. Even with the astigmatic cavity, however, the power fluctuations through the cavity were on the order of a few percent of the average transmitted power with the wavelength of the laser held constant. These fluctuations can be attributed to the extremely long coherence length of the ECDL (>2 km) and the small fluctuations of the laser power generation. These fluctuations occurred on a millisecond timescale, compared with the microsecond events observed for on-axis alignment. Larger diameter mirrors and larger mirror spot patterns could be used to increase the power stability in the cavity. Despite these fluctuations, the cavity transmission output is remarkably stable to amplitude fluctuations.

Stable power output from the cavity could be achieved by slightly modulating the laser wavelength to produce a 150 MHz frequency modulation. Aside from modest intensity spikes occurring near the turning points of the sine wave, where the laser end mirror is momentarily stationary, stable power transmission can be observed. Scanning the laser at a rate exceeding 1 $cm^{-1}$/s eliminated all traces of cavity resonances, even with a detection bandwidth exceeding 100 kHz, which implies an effective cavity mode spacing on the order of 3 MHz. This estimate assumes that scanning the laser through several free spectral ranges within the ringdown time is sufficient to suppress resonant energy buildup in the cavity.

B. OA-CR

With the chopper wheel 14 spinning, the buildup-ringdown events 25 and 26 occur at a high repetition rate, in this case chosen to be 3 kHz (FIG. 4). An average (curve 27) of 20 individual decays 26 is shown in FIG. 5, which exhibits a smooth exponential function. (The natural logarithm 28 of the signal 27 is linear.) Scanning the laser frequency produces an absorption spectrum. The signal sensitivity and analysis is identical to existing cavity ring down techniques however the OA approach does not require that the laser frequency match one of the cavity longitudinal modes. This is a significant advantage since data can be collected in real time and without the need to wait for a resonance to occur. As expected, this system was found to be largely insensitive to vibrations and slight changes in alignment.

C. OA-I

To record an Off-Axis ICOS spectrum, the output wavelength of the laser beam 11 from laser 10 is scanned over a small frequency interval (1.5 $cm^{-1}$ in the example shown here) at a repetition rate of 20 Hz with the light beam chopping 14 deactivated. The noise level during a single sweep corresponded to fractional absorption of less than ~1 ppm such that the absorption feature could be easily observed in real time with a 0.05 second update interval. This line strength of this $CO_2$ absorption line is equal to $3\times10^{-7}$ per cm. The data shown in FIG. 6 displays the sweep averaged Off-Axis ICOS output signal over a range of 0.6 $cm^{-1}$ in which an absorption arising from carbon dioxide in 90 Torr ambient air is clearly seen. A single scan was acquired in only 20 milliseconds and a baseline was taken by blocking the laser. FIG. 6 corresponds to average over 256 traces. The 0.6 cm$^{-1}$ scan shown in the figure required 3.6 seconds to acquire. A fit was performed on the averaged scan with the residuals displayed above. The noise on the residual away from the peak is about 0.2 mV. The total signal is approximately 130 mV, giving a signal to noise level of 130/0.2=650:1. Giving due consideration to the 20 Hz scanning frequency and the 10 k low-pass signal filtering, this gives an absorption sensitivity level of $2\times10^{-10}$ cm$^{-1}$ Hz$^{-1/2}$.

This patent describes in detail the innovative aspects of OA-CR and OA-I, as well as the significance of the invention as related to spectroscopic methods. In addition to disclosing the unique combination of off-axis cavity alignment with both CRDS and ICOS for the purpose of determining the optical loss within the cavity due to molecular absorption, we have presented data obtained with an instrument constructed by the inventors which reduces to practice key features and capabilities of the OA-CR and OA-I methods.

What is claimed is:

1. An absorption spectroscopy instrument with off-axis cavity alignment, comprising:
   an arrangement of two or more mirrors forming a stable optical cavity, the cavity mirror arrangement defining an axial light path in the resonant cavity wherein each reflection at each mirror thereof occurs at substantially the same spot for said axial light path, the cavity mirror arrangement also defining off-axis light paths in the optical cavity wherein successive reflections at any given mirror thereof occur at different locations for any off-axis light path, the cavity adapted to receive an absorption cell with a sample to be tested;
   a light source providing a light beam that is introduced into the optical cavity through a partially transmissive mirror of the cavity, the light beam being directed along any off-axis light path in the resonant cavity;
   a detector situated in a position to receive and measure a portion of the light beam from the resonant cavity; and
   means for processing data representing the light measurement from the detector for analyzing a sample received by said optical cavity.

2. The instrument of claim 1 wherein said optical cavity is a two-mirror cavity.

3. The instrument of claim 1 wherein said optical cavity is a ring cavity.

4. The instrument of claim 1 wherein said optical cavity contains at least one mirror with a spherical reflecting surface curvature.

5. The instrument of claim 1 wherein said optical cavity is arranged to form a stable resonant cavity in which the mirror separation is greater than, or equal to, a confocal cavity arrangement and the mirror separation is less than the sum of the radii of the cavity optics.

6. The instrument of claim 1 wherein said optical cavity contains at least one mirror that has an astigmatic reflecting surface curvature.

7. The instrument of claim 1 wherein said absorption cell is a low-scatter sample gas flow arrangement passing through the off-axis light path of said cavity for measurement of trace chemical species in a gas sample.

8. The instrument of claim 1 further comprising means for modulating the intensity of the light beam introduced from the source into the optical cavity in a manner designed to obtain from the decay rate of the intra-cavity light, a measurement of OA-CR absorption signal by a sample received within the resonant cavity.

9. The instrument of claim 1 further comprising means for modulating the wavelength of the light beam introduced from the source into the optical cavity in a manner designed to obtain from the transmitted light measurement of said detector, a measurement of OA-I absorption signal by a sample received within the resonant cavity.

10. The instrument of claim 1 wherein said light source is any wavelength tunable light source producing a measurable transmitted signal.

11. The instrument of claim 10 wherein the light source is selected from the group consisting of filtered light sources, tunable lasers, and lamps.

12. The instrument of claim 1 wherein the light source is characterized by modulated output power.

13. The instrument of claim 12 wherein the light source is modulated by means of a modulated drive current input.

14. The instrument of claim 1 wherein a direct optical chopping element is situated in the path of the light beam between the light source and the cavity mirror arrangement.

15. The instrument of claim 14 wherein the chopping element is selected from the group consisting of a mechanical chopper, an acousto-optic modulator, an electro-optic modulator.

16. The instrument of claim 1 wherein the detector is positioned to receive light exiting the cavity through one of the mirrors thereof.

17. An absorption spectroscopy instrument with off-axis cavity alignment, comprising:
   a stable optical cavity defined by a pair of mirrors with reflectivities of the mirrors being at least 0.5 and with a mirror separation which is greater than or equal to a confocal cavity arrangement and also less than the sum of the radii of curvature of the two mirrors, the pair of mirrors defining an axial light path in the optical cavity wherein each reflection at each mirror thereof occurs at substantially the same spot for said axial light path, the pair of mirrors further defining off-axis light paths in the optical cavity wherein successive reflections at any given mirror thereof occur at different locations for any off-axis light path, the optical cavity adapted to receive a sample to be tested;
   a light source providing a light beam that is introduced into the optical cavity through a partially transmissive mirror of the cavity, the light beam being directed along any off-axis light path in the optical cavity;
   a detector situated in a position to receive and measure a portion of the light beam exiting the optical cavity through one of the mirrors; and
   means for processing data representing the light measurement from the detector for analyzing a sample received by said optical cavity.

18. The instrument of claim 17 wherein each mirror has a spherical reflecting surface curvature.

19. The instrument of claim 17 wherein at least one of the mirrors has an astigmatic reflecting surface curvature.

20. The instrument of claim 17 wherein a low-scatter sample gas flow arrangement passes through the off-axis light path of said cavity for measurement of trace chemical species in a gas sample.

21. The instrument of claim 17 further comprising means for modulating the intensity of the light beam introduced from the source into the optical cavity in a manner designed to obtain from the decay rate of the intra-cavity light, a measurement of OA-CR absorption signal by a sample received within the resonant cavity.

22. The instrument of claim 17 further comprising means for modulating the wavelength of the light beam introduced from the source into the optical cavity in a manner designed to obtain from the transmitted light measurement of said detector, a measurement of OA-I absorption signal by a sample received within the resonant cavity.

23. The instrument of claim 17 wherein said light source is any wavelength tunable light source producing a measurable transmitted signal.

24. The instrument of claim 23 wherein the light source is selected from the group consisting of filtered light sources, tunable lasers, and lamps.

25. The instrument of claim 17 wherein the light source is characterized by modulated output power.

26. The instrument of claim 25 wherein the light source is modulated by means of a modulated drive current input.

27. The instrument of claim 17 wherein a direct optical chopping element is situated in the path of the light beam between the light source and the cavity mirror arrangement.

28. The instrument of claim 27 wherein the chopping element is selected from the group consisting of a mechanical chopper, an acousto-optic modulator, an electro-optic modulator.

29. The instrument of claim 17 wherein the detector is positioned to receive light exiting the cavity through one of the mirrors thereof.

30. An absorption spectroscopy method, comprising:
injecting a light beam into an arrangement of mirrors that is arranged to form a stable optical cavity, the cavity arrangement adapted to receive a sample to be tested, the light beam being introduced through a partially transmissive mirror into the resonant cavity along any off-axis light path thereof wherein successive reflections at any given mirror of the optical cavity occur at different locations on that mirror;
measuring light from the optical cavity; and
processing light measurement data to obtain an analysis of a sample received by the optical cavity.

31. The method of claim 30 further comprising modulating the intensity of the light beam introduced from the light source into the optical cavity in a manner designed to obtain from the decay rate of the intra-cavity light, a measurement of OA-CR absorption signal by a sample received within the resonant cavity.

32. The method of claim 31 wherein the intensity modulation is such that the fall time of the intensity is substantially shorter than the cavity ringdown time, while the repetition cycle time is longer than the ringdown time.

33. The method of claim 31 wherein the intensity is modulated by chopping the light signal produced by the light source.

34. The method of claim 31 wherein the intensity is modulated by controlling the amount of light produced by the source.

35. The method of claim 30 further comprising modulating the wavelength of the light beam introduced from the light source into the optical cavity in a manner designed to obtain from the transmitted light measurement of said detector, a measurement of OA-I absorption signal by a sample received within the resonant cavity.

36. The method of claim 35 wherein the modulating includes dithering the light wavelength about a selected wavelength.

37. The method of claim 30 wherein a low-scatter sample flow configuration directs a flow of sample across the off-axis light path of the laser light beam within the optical cavity.

38. The method of claim 30 wherein the arrangement of mirrors forms a stable optical cavity.

39. The method of claim 38 wherein each of the mirrors has a spherical surface curvature.

40. The method of claim 38 wherein at least one of the mirrors has an astigmatic surface curvature.

* * * * *